United States Patent [19]

Hierstetter et al.

[11] Patent Number: 5,990,334
[45] Date of Patent: Nov. 23, 1999

[54] IONIC ORGANOSILICON COMPOUNDS AND THEIR PREPARATION AND USE

[75] Inventors: Thomas Hierstetter; Jochen Dauth; Birgit Peschanel; Bernward Deubzer, all of Burghausen, Germany

[73] Assignee: Wacker-Chemie GmbH, Munich, Germany

[21] Appl. No.: 08/987,727

[22] Filed: Dec. 9, 1997

[30] Foreign Application Priority Data

Dec. 10, 1996 [DD] German Dem. Rep. .......... 196 51 287

[51] Int. Cl.$^6$ .................................. C07F 7/08; C07F 7/10
[52] U.S. Cl. .................. 556/413; 556/405; 556/418; 556/419; 556/420; 556/424; 556/425; 556/428
[58] Field of Search .................. 556/413, 405, 556/418, 419, 420, 425, 424, 428

[56] References Cited

U.S. PATENT DOCUMENTS

| | | | |
|---|---|---|---|
| 3,734,763 | 5/1973 | Plueddemann | 556/413 |
| 3,779,912 | 12/1973 | Redmore et al. | |
| 3,819,675 | 6/1974 | Plueddemann | 556/413 |
| 4,493,926 | 1/1985 | Williams et al. | 556/424 |
| 4,496,705 | 1/1985 | Florence et al. | 556/413 |
| 4,525,567 | 6/1985 | Campbell et al. | |
| 4,654,161 | 3/1987 | Kollmeier et al. | 556/420 |
| 4,898,614 | 2/1990 | Halloran et al. | 556/413 |
| 4,918,210 | 4/1990 | Fenton et al. | 556/425 |
| 5,041,590 | 8/1991 | Snow | 558/425 |
| 5,068,380 | 11/1991 | Meguriya et al. | 556/428 |
| 5,073,619 | 12/1991 | O'Lenick | 556/413 |
| 5,087,715 | 2/1992 | Snow | 556/413 |
| 5,246,607 | 9/1993 | Schaefer et al. | 556/413 |
| 5,344,949 | 9/1994 | Koerner et al. | 556/413 |
| 5,399,737 | 3/1995 | Park et al. | 556/413 |
| 5,405,983 | 4/1995 | Fost et al. | |
| 5,532,399 | 7/1996 | Hager et al. | |

FOREIGN PATENT DOCUMENTS

| | | |
|---|---|---|
| 0095156 | 5/1983 | European Pat. Off. |
| 0292760 | 11/1988 | European Pat. Off. |
| 0423696 | 4/1991 | European Pat. Off. |
| 9518096 | 12/1994 | WIPO |
| 9632436 | 4/1996 | WIPO |

OTHER PUBLICATIONS

M. Litt and T. Matsuda, J. Appl. Polym. Sci. 19 (1975) 1221.

Primary Examiner—Paul F. Shaver
Attorney, Agent, or Firm—Brooks & Kushman P.C

[57] ABSTRACT

Ionic organosilicon compounds comprising siloxane units of the formula $$A_aR_bX_cSiO_{(4-a-b-c)/2} \quad (I),$$

in which

R is an identical or different, optionally halogenated hydrocarbon radicals having 1 to 12 carbon atoms or radicals of the formulae $$-R'-((NHCH_2CH_2)_o-(N^+H_2CH_2CH_2)_p-N^{(x+q-2)+}H_xR''_q)_{d-1} \quad (II)$$

$$-R'-(SH)_{d-1} \quad (III)$$

or $$-R'-(Z-C(O)-CR'''=CH_2)_{d-1} \quad (IV)$$

in which

R', R", Z, R''', o, p, q, x, d, X and A have the meaning given in claim 1 and a is 0 or 1, b is 0, 1, 2 or 3, c is 0, 1, 2 or 3 and the sum a+b+c is≦4, with the proviso that at least one radical A is contained in each molecule, and, optionally, non-bonding counter-ions from the group consisting of alkali metal, alkaline earth metal and ammonium ions of organic amines are present to compensate the negative charges and non-bonded counterions from the group consisting of organic anions, such as, for example, acetate ions, are present to compensate the positive charges,their preparation and their use.

9 Claims, No Drawings

IONIC ORGANOSILICON COMPOUNDS AND THEIR PREPARATION AND USE

BRIEF SUMMARY OF THE INVENTION

The present invention relates to ionic organosilicon compounds and their preparation and use.

BACKGROUND OF THE INVENTION

According to M. Litt and T. Matsuda, J. Appl. Polym. Sci. 19 (1975) 1221, zwitterionic sulfonate-containing siloxanes are obtained by reaction of aminoalkyl functional silanes/siloxanes with ω-alkyl sultones. Although ω-alkyl sultones are reactive, as a rule they are also toxic and carcinogenic. Such compounds can be used only in special plants with high safety regulations. Use of the zwitterionic siloxanes obtained by this process is highly undesirable because of the residual content of ω-alkylsultones.

In U.S. Pat. No. 5,532,399 (Wacker-Chemie GmbH, issued on Jul. 2, 1996), ionic siloxanes are prepared by first producing via a nucleophilic substitution by sulfite ions on chloropropylsilanes and simultaneous hydrolysis, a sulfonate-functional siloxane hydrolysate, from which a sulfonic acid-functional siloxane hydrolysate is formed by acidification, which finally can be equilibrated with amine-functional silanes/siloxanes and further siloxanes to give a zwitterionic siloxane which carries ammonium and sulfonate groups.

DETAILED DESCRIPTION OF THE INVENTION

The present invention relates to ionic organosilicon compounds comprising siloxane units of the formula $$A_a R_b X_c SiO_{(4-a-b-c)/2} \quad (I),$$

in which

R is an identical or different, optionally halogenated hydrocarbon radical having 1 to 12 carbon atoms or a radical of the formulae $$—R'—((NHCH_2CH_2)_o—(N^+H_2CH_2CH_2)_p—N^{(x+q-2)+}H_xR''_q)_{d-1} \quad (II),$$

$$—R'—(SH)_{d-1} \quad (III),$$

or $$—R'—(Z—C(O)—CR'''=CH_2)_{d-1} \quad (IV)$$

in which

R' is an identical or different di-, tri- or tetravalent hydrocarbon radical having 1 to 60 carbon atoms, which can be interrupted by one or more oxygen atoms, R'' is a hydrogen atom or an alkyl radical having 1 to 8 carbon atoms, Z is an oxygen atom or a radical of the formula R''' is a hydrogen atom or a methyl radical, o is 0 or an integer from 1 to 100, p is 0 or an integer from 1 to 100, q is 0, 1 or 2, x is 0, 1 or 2 and d is 2, 3 or 4, depending on the valency of R', with the proviso that in formula (II) the sum x+q is 2 or 3, X is an identical or different halogen atom or a radical of the formula —OR¹, where R¹ is an alkyl radical which can be interrupted by an oxygen atom, or a radical of the formula $$—R^2—((CH_2CH_2O)_k—(CH(CH_3)CH_2O)_l—((CH_2)_4O)_m—R^3)_e(V)$$

in which

R² is a di-, tri- or tetravalent hydrocarbon radical having 1 to 60 carbon atoms, which can be interrupted by one or more oxygen atoms and is substituted by one or more groups of the formulae

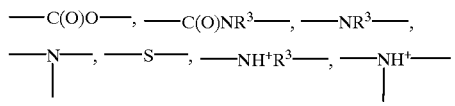

in which

R³ is a hydrogen atom or a hydrocarbon radical having 1 to 30 carbon atoms, which can optionally be interrupted by a group of formula —CO—, k is 0 or an integer from 1 to 100, l is 0 or an integer from 1 to 100, m is 0 or an integer from 1 to 100 and e is 2, 3 or 4, depending on the valency of R², with the proviso that the sum of k+l+m ≧1, and A is a radical of the formula $$—R^4—B_{(f-1)} \quad (VI)$$

in which

R⁴ has the meanings given above for R², f is 2, 3 or 4, depending on the valency of R⁴, and B is a radical of the formulae

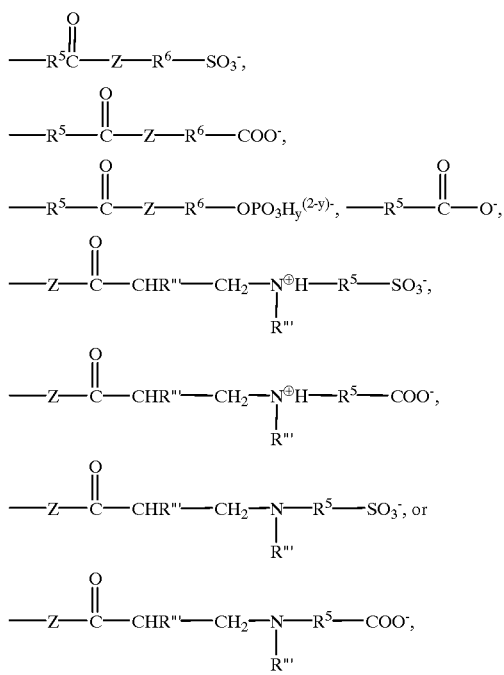

in which

R⁵ is an identical or different divalent hydrocarbon radical having 2 to 18 carbon atoms, R⁶ is an identical or different divalent alkylene radical having 1 to 18 carbon atoms or a radical of the formulae

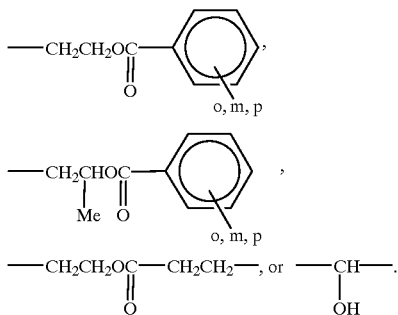

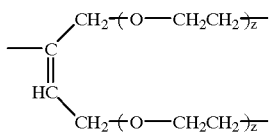

where
  Me is the methyl radical,
  Z and R′″ in each case have one of the meanings given above for these radicals and
  y is 0 or 1,
  a is 0 or 1,
  b is 0, 1, 2 or 3,
  c is 0, 1, 2 or 3
and the sum a+b+c is ☐ 4,
with the proviso that at least one radical A is contained in each molecule, and, optionally, non-bonding counter-ions from the group consisting of alkali metal, alkaline earth metal and ammonium ions of organic amines are present for compensating the negative charges and non-bonded counter-ions from the group consisting of organic anions, such as, for example, acetate ions, are present for compensating the positive charges.

The organosilicon compounds according to the invention are those which consist of units of formulae (I).

The organosilicon compounds according to the invention can be any desired organosilicon compounds, such as, organosilanes, as well as linear, branched and cyclic organosiloxanes, siloxanes being preferred.

Examples of R are alkyl radicals, such as the methyl, ethyl, n-propyl, iso-propyl, 1-n-butyl, 2-n-butyl, iso-butyl, tert-butyl, n-pentyl, iso-pentyl, neo-pentyl and tert-pentyl radical; hexyl radicals, such as the n-hexyl radical; heptyl radicals, such as the n-heptyl radical; octyl radicals, such as the n-octyl radical and iso-octyl radicals, such as the 2,2,4-tri-methylpentyl radical; nonyl radicals, such as the n-nonyl radical; decyl radicals, such as the n-decyl radical; dodecyl radicals, such as the n-dodecyl radical; and octadecyl radicals, such as the n-octadecyl radical; cycloalkyl radicals, such as the cyclopentyl, cyclohexyl and cycloheptyl radical and methylcyclohexyl radicals; alkenyl radicals, such as the vinyl, 1-propenyl and the 2-propenyl radical; aryl radicals, such as the phenyl, naphthyl, anthryl and phenanthryl radical; alkaryl radicals, such as o-, m- and p-tolyl radicals, xylyl radicals and ethylphenyl radicals; and aralkyl radicals, such as the benzyl radical and the α- and the β-phenylethyl radical.

Examples of halogenated radicals R are haloalkyl radicals, such as the 3,3,3-trifluoro-n-propyl radical, the 2,2,2,2′,2′,2′-hexafluoroisopropyl radical, the heptafluoroisopropyl radical and haloaryl radicals, such as the o-, m- and p-chlorophenyl radical.

Examples of radicals R′ are linear or branched alkylene radicals, such as, for example, the 1,2-ethylene, 1,3-propylene, 1,2-propylene, 1,3-(2-methyl-propylene) and dimethylmethylene radical, or polyvalent hydrocarbon radicals which are interrupted by oxygen atoms, such as, those of the formula

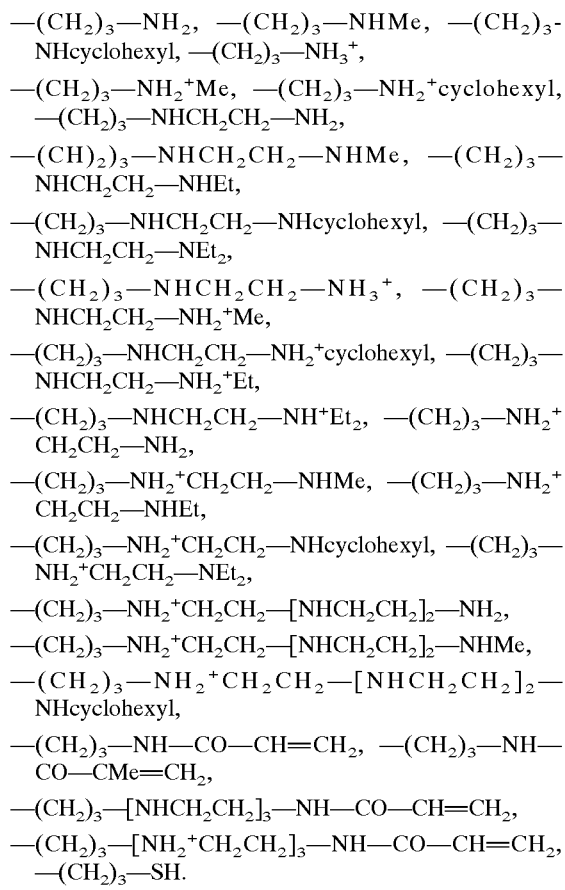

where z=0, 1, 2, 3, 4 or 5, the 1,3-propylene, 1,2-propylene and 1,3-(2-methyl-propylene) radical and radicals of formula (VII) being preferred and the 1,3-propylene radical being more preferred.

Examples of radicals R″ are the hydrogen atom and the examples mentioned for R as an alkyl radical having 1 to 8 carbon atoms, the hydrogen atom and the methyl radical being preferred and the hydrogen atom being more preferred.

The radical R′″ is preferably a hydrogen atom.

o is 0 or an integer from 1 to 30.

p is 0 or an integer from 1 to 30.

x is 1 or 2.

q is 0 or 1.

Examples of radicals R of the formulae (II) to (IV) are

—$(CH_2)_3$—$NH_2$, —$(CH_2)_3$—$NHMe$, —$(CH_2)_3$-$NHcyclohexyl$, —$(CH_2)_3$—$NH_3^+$, —$(CH_2)_3$—$NH_2^+Me$, —$(CH_2)_3$—$NH_2^+cyclohexyl$, —$(CH_2)_3$—$NHCH_2CH_2$—$NH_2$, —$(CH_2)_3$—$NHCH_2CH_2$—$NHMe$, —$(CH_2)_3$—$NHCH_2CH_2$—$NHEt$, —$(CH_2)_3$—$NHCH_2CH_2$—$NHcyclohexyl$, —$(CH_2)_3$—$NHCH_2CH_2$—$NEt_2$, —$(CH_2)_3$—$NHCH_2CH_2$—$NH_3^+$, —$(CH_2)_3$—$NHCH_2CH_2$—$NH_2^+Me$, —$(CH_2)_3$—$NHCH_2CH_2$—$NH_2^+cyclohexyl$, —$(CH_2)_3$—$NHCH_2CH_2$—$NH_2^+Et$, —$(CH_2)_3$—$NHCH_2CH_2$—$NH^+Et_2$, —$(CH_2)_3$—$NH_2^+CH_2CH_2$—$NH_2$, —$(CH_2)_3$—$NH_2^+CH_2CH_2$—$NHMe$, —$(CH_2)_3$—$NH_2^+CH_2CH_2$—$NHEt$, —$(CH_2)_3$—$NH_2^+CH_2CH_2$—$NHcyclohexyl$, —$(CH_2)_3$—$NH_2^+CH_2CH_2$—$NEt_2$,

—$(CH_2)_3$—$NH_2^+CH_2CH_2$—$[NHCH_2CH_2]_2$—$NH_2$,

—$(CH_2)_3$—$NH_2^+CH_2CH_2$—$[NHCH_2CH_2]_2$—$NHMe$,

—$(CH_2)_3$—$NH_2^+CH_2CH_2$—$[NHCH_2CH_2]_2$—$NHcyclohexyl$,

—$(CH_2)_3$—$NH$—$CO$—$CH=CH_2$, —$(CH_2)_3$—$NH$—$CO$—$CMe=CH_2$,

—$(CH_2)_3$—$[NHCH_2CH_2]_3$—$NH$—$CO$—$CH=CH_2$,

—$(CH_2)_3$—$[NH_2^+CH_2CH_2]_3$—$NH$—$CO$—$CH=CH_2$,

—$(CH_2)_3$—$SH$.

and

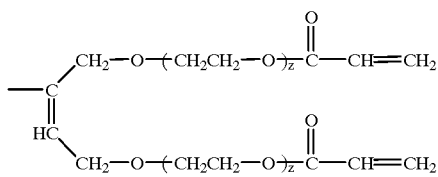

where
z has the meaning above,
and in which Me is the methyl radical and Et is the ethyl radical.

The radical R is preferably the methyl, ethyl, propyl, butyl, vinyl or cyclohexyl radical or a radical of the formula
—$(CH_2)_3$—$NH_2$, —$(CH_2)_3$—NHMe, —$(CH_2)_3$—$NH_3^+$,
—$(CH_2)_3$—$NH_2^+$Me, —$(CH_2)_3$—$NHCH_2CH_2$—$NH_2$,
—$(CH_2)_3$—$NHCH_2CH_2$—$NH_3^+$, —$(CH_2)_3$—$NH_2^+$ $CH_2CH_2$—$NH_2$, —$(CH_2)_3$—$NH_2^+CH_2CH_2$—NHMe,
—$(CH_2)_3$—SH and

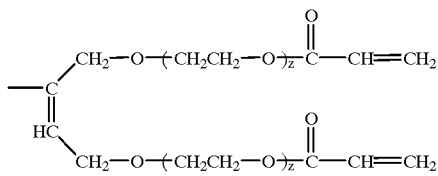

where Me is the methyl radical and z has the above mentioned meaning.

The radical R is more preferably the methyl, ethyl, propyl, butyl, vinyl or cyclohexyl radical, in particular the methyl radical.

Examples of radicals $R^1$ are the examples given for R as alkyl radicals, and the methoxyethyl and ethoxyethyl radical, the radical $R^1$ preferably being alkyl radicals having 1 to 4 carbon atoms, which can be interrupted by oxygen atoms, more preferably the methyl and the ethyl radical.

Examples of radicals $R^2$ are
—$(CH_2)_3$—$NHCH_2CH_2$—COO—, —$(CH_2)_3$—N$(CH_2CH_2$—COO—$)_2$,
—$(CH_2)_3$—N-cyclohexyl—$CH_2CH_2$—COO—,
—$(CH_2)_3$—$NHCH_2CH_2$—$NHCH_2CH_2$—COO—,

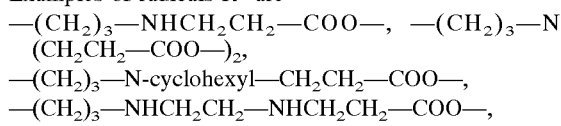

—$(CH_2)_3$—$SCH_2CH_2$—COO—, —$(CH_2)_3$—$NHCH_2CH_2$—COO—$CH_2CH_2$—,
—$(CH_2)_3$—N$(CH_2CH_2$—COO—$CH_2CH_2$—$)_2$,
$(CH_2)_3$—N-cyclohexyl—$CH_2CH_2$—COO—$CH_2CH_2$—,
—$(CH)_2)_3$—$NHCH_2CH_2$—$NHCH_2CH_2$—COO—$CH_2CH_2$—,

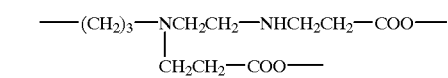

—$(CH_2)_3$—$SCH_2CH_2$—COO—$CH_2CH_2$—, —$(CH_2)_3$—$NH_2^+CH_2CH_2$—COO—,
—$(CH_2)_3$—$NH^+(CH_2CH_2$—COO—$)_2$ —$(CH_2)_3$—$NH+$—cyclohexyl—$CH_2CH_2$—COO—,

—$(CH_2)_3$—$NHCH_2CH_2$—$NH_2^+CH_2CH_2$—COO—,

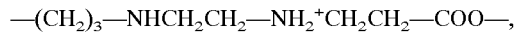

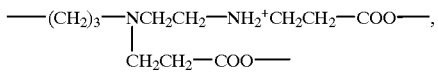

—$(CH_2)_3$—$NH_2^+CH_2CH_2$—COO—$CH_2CH_2$—,
—$(CH_2)_3$—$NH^+(CH_2CH_2$—COO—$CH_2CH_2$—$)_2$,
—$(CH_2)_3$—$NH^+$—cyclohexyl—$CH_2CH_2$—COO—$CH_2CH_2$—,
—$(CH_2)_3$—$NH_2^+CH_2CH_2$—$NHCH_2CH_2$—COO—$CH_2CH_2$—,

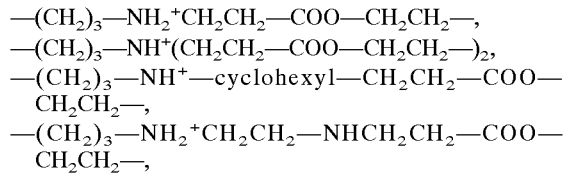

and

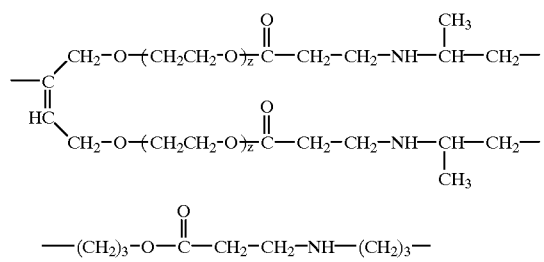

where z has the above mentioned meaning.

The radical $R^2$ is preferably
—$(CH_2)_3$—$NHCH_2CH_2$—COO—, —$(CH_2)_3$—N$(CH_2CH_2$—COO—$)_2$,
—$(CH_2)_3$—$NHCH_2CH_2$—$NHCH_2CH_2$—COO—,

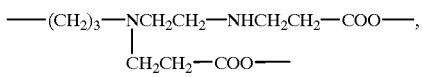

—$(CH_2)_3$—$NHCH_2CH_2$—COO—$CH_2CH_2$—,
—$(CH_2)_3$—N$(CH_2CH_2$—COO—$CH_2CH_2$—$)_2$,
—$(CH_2)_3$—$NHCH_2CH_2$—$NHCH_2CH_2$—COO—$CH_2CH_2$—,

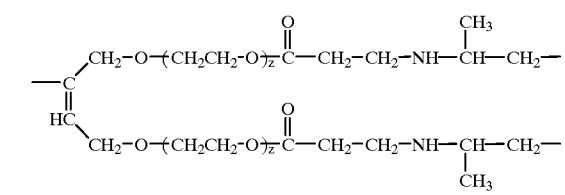

where z has the above mentioned meaning.

Examples of $R^3$ are the examples given for R for hydrocarbon radicals having 1 to 20 carbon atoms, and —CO—$CH_3$, —CO—$CH_2$—$CH_3$ and —CO-butyl.

The radical $R^3$ is preferably a hydrogen atom or a methyl or butyl group.

Examples of X as radicals of the formula (V) are
—$(CH_2)_3$—NH—$CH_2$—$CH_2$—CO—$(OC_2H_4)_9OCH_3$, —(CH$_2$)$_3$—NH—CH$_2$—CH$_2$—CO—(OC$_2$H$_4$)$_6$OC$_6$H$_5$ and —(CH$_2$)$_3$—NH—CH$_2$—CH$_2$—CO—(OC$_2$H$_4$)$_{16}$OC$_6$H$_4$-p-C$_9$H$_{19}$, where —(CH$_2$)$_3$—NH—CH$_2$—CH$_2$—CO—(OC$_2$H$_4$)$_9$OCH$_3$ is preferred.

The value for k+l+m is between 2 and 30, more preferably between 4 and 20.

If X has the meaning of a halogen atom, it is preferably the chlorine atom.

X is the radical —OR$^1$, where R$^1$ has the above mentioned meaning, —OCH$_3$ and —OC$_2$H$_5$ being preferred.

Examples of radicals R$^4$ are

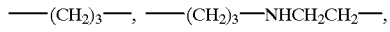
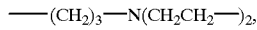
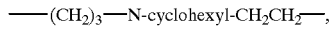
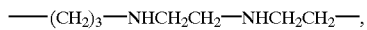
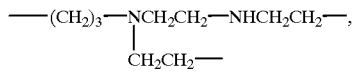
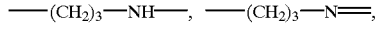
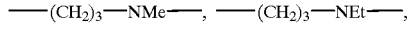
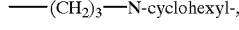
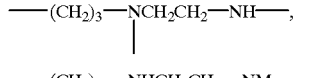
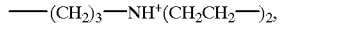
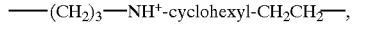
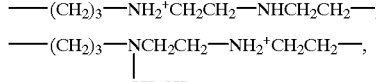
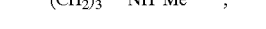
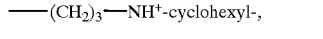
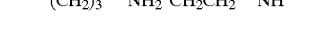
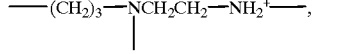
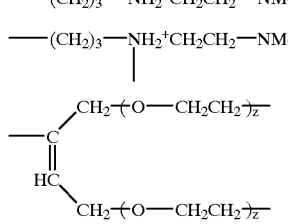

where z has the above mentioned meaning and Me is the methyl radical and Et is the ethyl radical.

Examples of the radical R$^5$ are the linear or branched alkylene radicals mentioned above for R', the ethylene and 1,2-propylene radical being preferred and the ethylene radical being more preferred.

Examples of the radical R$^6$ as alkylene radicals are the methylene radical, ethylene radical, 1,3-propylene radical, 2-propylene and 1,3-(2-methylpropylene) radical, n-butylene radical and 2-n-butylene, iso-butylene, n-pentylene, iso-pentylene and the n-hexylene radical.

The radical R$^6$ is preferably the ethylene radical, the 1,3-propylene radical, —(CH$_3$)$_2$C—CH$_2$— and radicals of the formula

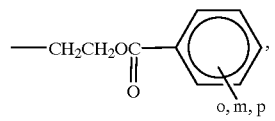
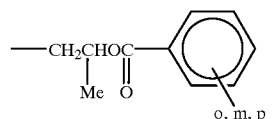
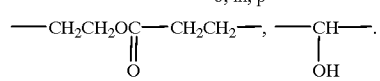

where Me is the methyl radical, and where the —(Me)$_2$C—CH$_2$—radical and a radical of the formulae

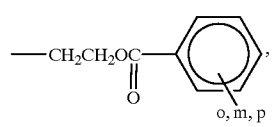
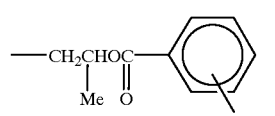
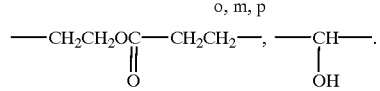

are more preferred.

Examples of the radical Z are the oxygen atom and radicals of the formulae —NH—, —NCH$_3$—, —NCH$_2$CH$_3$— and —NCH$_2$CH$_2$CH$_3$—, the oxygen atom and the radical —NH— being preferred and the radical —NH— being more preferred.

Examples of the radical B are

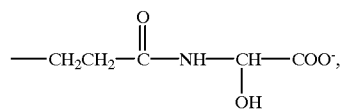
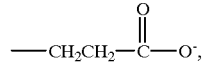
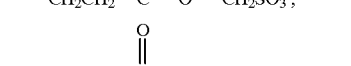
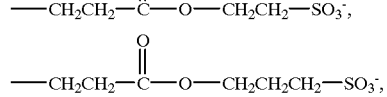

-continued $-CH_2CH_2-\underset{\underset{O}{\|}}{C}-O-\underset{\underset{CH_3}{|}}{\overset{\overset{CH_3}{|}}{C}}-CH_2-SO_3^-,$ $-CH_2CH(Me)-\underset{\underset{O}{\|}}{C}-O-CH_2-SO_3^-,$ $-CH_2CH(Me)-\underset{\underset{O}{\|}}{C}-O-CH_2CH_2-SO_3^-,$ $-CH_2CH(Me)-\underset{\underset{O}{\|}}{C}-O-CH_2CH_2CH_2-SO_3^-,$ $-CH_2CH(Me)-\underset{\underset{O}{\|}}{C}-O-\underset{\underset{CH_3}{|}}{\overset{\overset{CH_3}{|}}{C}}-CH_2-SO_3^-,$ $-CH_2CH_2-\underset{\underset{O}{\|}}{C}-O-CH_2-COO^-,$ $-CH_2CH_2-\underset{\underset{O}{\|}}{C}-O-CH_2CH_2-COO^-,$ $-CH_2CH_2-\underset{\underset{O}{\|}}{C}-O-CH_2CH_2CH_2-COO^-,$ $-CH_2CH_2-\underset{\underset{O}{\|}}{C}-O-\underset{\underset{CH_3}{|}}{\overset{\overset{CH_3}{|}}{C}}CH_2-COO^-,$ $-CH_2CH(Me)-\underset{\underset{O}{\|}}{C}-O-CH_2-COO^-,$ $-CH_2CH(Me)-\underset{\underset{O}{\|}}{C}-O-CH_2CH_2-COO^-,$ $-CH_2CH(Me)-\underset{\underset{O}{\|}}{C}-O-CH_2CH_2CH_2-COO^-,$ $-CH_2CH(Me)-\underset{\underset{O}{\|}}{C}-O-\underset{\underset{CH_3}{|}}{\overset{\overset{CH_3}{|}}{C}}CH_2-COO^-,$ $-CH_2CH_2-\underset{\underset{O}{\|}}{C}-NH-CH_2-OPO_3^{2-},$ $-CH_2CH_2-\underset{\underset{O}{\|}}{C}-NH-CH_2CH_2OPO_3^{2-},$ $-CH_2CH_2-\underset{\underset{O}{\|}}{C}-NH-CH_2CH_2CH_2OPO_3^{2-},$ $-CH_2CH^2-\underset{\underset{O}{\|}}{C}-NH-\underset{\underset{CH_3}{|}}{\overset{\overset{CH_3}{|}}{C}}CH_2OPO_3^{2-},$ $-CH_2CH(Me)-\underset{\underset{O}{\|}}{C}-NH-CH_2OPO_3^{2-},$ $-CH_2CH(Me)-\underset{\underset{O}{\|}}{C}-NH-CH_2CH_2OPO_3^{2-},$ $-CH_2CH(Me)-\underset{\underset{O}{\|}}{C}-NH-CH_2CH_2CH_2OPO_3^{2-},$ -continued $-CH_2CH(Me)-\underset{\underset{O}{\|}}{C}-NH-\underset{\underset{CH_3}{|}}{\overset{\overset{CH_3}{|}}{C}}CH_2OPO_3^{2-},$ $-CH_2CH_2-\underset{\underset{O}{\|}}{C}-O-CH_2CH_2O\underset{\underset{O}{\|}}{C}CH_2CH_2SO_3^-,$ $-CH_2CH_2-\underset{\underset{O}{\|}}{C}-O-CH_2CH_2O\underset{\underset{O}{\|}}{C}CH_2CH_2COO^-,$ $-CH_2CH-\underset{\underset{O}{\|}}{\underset{|}{C}}-O-CH_2CH_2O\underset{\underset{O}{\|}}{C}CH_2CH_2SO_3^-,$
  $\phantom{-CH_2}CH_3$ $-CH_2CH-\underset{\underset{O}{\|}}{\underset{|}{C}}-O-CH_2CH_2O\underset{\underset{O}{\|}}{C}CH_2CH_2COO^-,$
  $\phantom{-CH_2}CH_3$ $-CH_2CH_2-\underset{\underset{O}{\|}}{C}-O-CH_2CH_2O\underset{\underset{O}{\|}}{C}-\underset{\underset{COO^-}{}}{\bigcirc},$ $-CH_2CH_2-\underset{\underset{O}{\|}}{C}-O-CH_2CHO\underset{\underset{O}{\|}}{C}-\underset{\underset{COO^-}{}}{\bigcirc},$
  $\phantom{-CH_2CH_2-C-O-CH_2}CH_3$ $-CH_2CH_2-\underset{\underset{O}{\|}}{C}-O-CH_2CH_2O\underset{\underset{O}{\|}}{C}-\bigcirc-COO^-,$ $-CH_2CH_2-\underset{\underset{O}{\|}}{C}-O-CH_2CHO\underset{\underset{O}{\|}}{C}-\bigcirc-COO^-,$
  $\phantom{-CH_2CH_2-C-O-CH_2}CH_3$ $-CH_2CH_2-\underset{\underset{O}{\|}}{C}-O-CH_2CH_2O\underset{\underset{O}{\|}}{C}-\bigcirc-COO^-,$ $-CH_2CH_2-\underset{\underset{O}{\|}}{C}-O-CH_2CHO\underset{\underset{O}{\|}}{C}-\bigcirc-COO^-,$
  $\phantom{-CH_2CH_2-C-O-CH_2}CH_3$ $-CH_2CH_2-\underset{\underset{O}{\|}}{C}-O-CH_2CH_2O\underset{\underset{O}{\|}}{C}CH_2CH_2-OPO_3^{2-},$ $-CH_2CH_2-\underset{\underset{O}{\|}}{C}-NH-CH_2-SO_3^-,$ $-CH_2CH_2-\underset{\underset{O}{\|}}{C}-NH-CH_2CH_2-SO_3^-,$ $-CH_2CH_2-\underset{\underset{O}{\|}}{C}-NH-CH_2CH_2CH_2-SO_3^-$

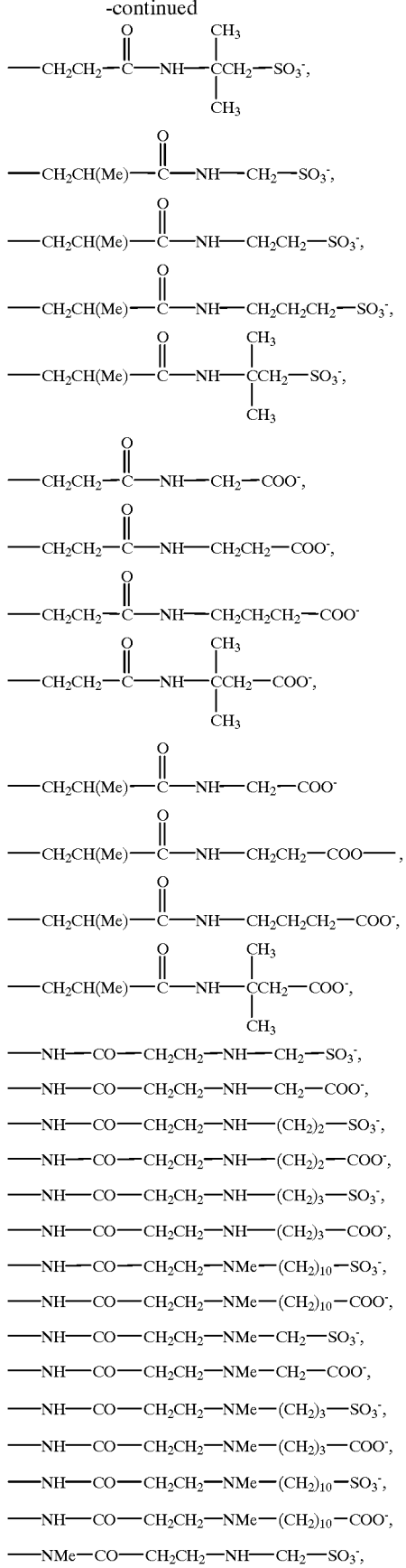
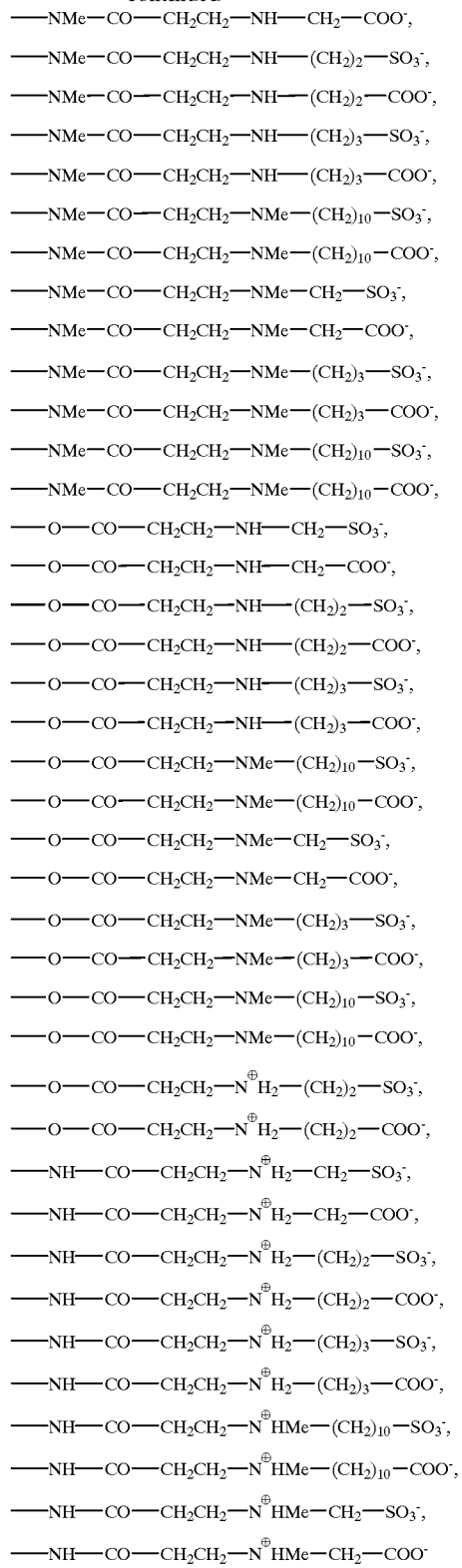
where Me is the methyl radical.
Examples of the ionic organosilicon compounds according to the invention are those which are built up
a) from $Me_3SiO_{1/2}$—, $Me_2SiO$—, —$OMeSi(CH_2)_3$—$N^+H_2$—$(CH_2)_2$—$CO$—$NH$—$C(Me)_2$—$CH_2$—$SO_3^-$ b) from $Me_2SiO-$, $-_{1/2}OMe_2Si\ (CH_2)_3-N^+H_2-(CH_2)_2\ CO-NH-C\ (Me)_2-CH_2-SO_3^-$ c) from $Me_3SiO_{1/2}-$, $Me_2SiO-$, $-OMeSi\ (CH_2)_3N^+Hcycl.\ Hex-(CH_2)_2-CONHC\ (Me)_2CH_2SO_3^-$ d) from $Me_2SiO-$, $-_{1/2}OMe_2Si\ (CH_2)_3N^+Hcycl.Hex-(CH_2)_2-CONHC\ (Me)_2CH_2SO_3^-$ e) from $Me_3SiO_{1/2}-$, $Me_2SiO-$, $-OMeSi\ (CH_2)_3N^+HMe-(CH_2)_2-CONHC\ (Me)_2CH_2SO_3-$ f) from $Me_2SiO-$, $-_{1/2}OMe_2Si\ (CH_2)_3N^+HMe-(CH_2)_2-CONHC\ (Me)_2CH_2SO_3^-$ g) from $Me_3SiO_{1/2}-$, $Me_2SiO-$, $-OMeSi(CH_2)_3-N^+H_2-(CH_2)_2-CO-NH-CH_2-CH_2-SO_3^-$ h) from $Me_2SiO-$, $-_{1/2}OMe_2Si\ (CH_2)_3-N^+H_2-(CH_2)_2-CO-NH-CH_2-CH_2-SO_3^-$ i) from $Me_3SiO_{1/2}-$, $Me_2SiO-$, $-OMeSi\ (CH_2)_3N^+Hcycl.Hex-(CH_2)_2-CONHCH_2CH_2SO_3^-$ j) from $Me_2SiO-$, $-_{1/2}OMe_2Si\ (CH_2)_3N^+Hcycl.Hex-(CH_2)_2-CONHCH_2CH_2SO_3^-$ k) from $Me_3SiO_{1/2}-$, $Me_2SiO-$, $-OMeSi\ (CH_2)_3N^+HMe-(CH_2)_2-CONHCH_2CH_2SO_3^-$ l) from $Me_2SiO-$, $-_{1/2}OMe_2Si\ (CH_2)_3N^+HMe-(CH_2)_2-CONHCH_2CH_2SO_3^-$ m) from $Me_3SiO_{1/2}-$, $Me_2SiO-$, $-OMeSi\ (CH_2)_3N^+H_2-(CH_2)_2-COOCH_2CH_2OOCCH_2CH_2-SO3^-$ n) from $Me_2SiO-$, $-_{1/2}OMe_2Si\ (CH_2)_3N^+H_2-(CH_2)_2-COOCH_2CH_2OOCCH_2CH_2-SO_3^-$ o) from $Me_3SiO_{1/2}-$, $Me_2SiO-$, $-OMeSi\ (CH_2)_3N^+H_2-(CH_2)_2-COOCH_2CH_2OOCCH_2CH_2-COO^-$ p) from $Me_2SiO-$, $-_{1/2}OMe_2Si\ (CH_2)_3N^+H_2-(CH_2)_2\ COOCH_2CH_2OOCCH_2CH_2-COO^-$ q) from $Me_3SiO_{1/2}-$, $Me_2SiO-$, $-OMeSi\ (CH_2)_3N^+HMe-(CH_2)_2-COOCH_2CH_2OOCCH_2CH_2-SO_3^-$ r) from $Me_2SiO-$, $-_{1/2}OMe_2Si\ (CH_2)_3N^+HMe-(CH_2)_2-COOCH_2CH_2OOCCH_2CH_2-SO_3^-$ s) from $Me_3SiO_{1/2}-$, $Me_2SiO-$, $-OMeSi\ (CH_2)_3N^+HMe-(CH_2)_2-COOCH_2CH_2OOCCH_2CH_2-COO^-$ t) from $Me_2SiO-$, $-_{1/2}OMe_2Si\ (CH_2)_3N^+HMe-(CH_2)_2-COOCH_2CH_2OOCCH_2CH_2-COO^-$ u) from $Me_3SiO_{1/2}-$, $Me_2SiO-$, $-OMeSi\ (CH_2)_3-N+H_2-(CH_2)_2-CO-NH-C\ (Me)_2-CH_2-OPO_3^{2-}$ v) from $Me_2SiO-$, $-_{1/2}OMe_2Si\ (CH_2)_3-N^+H_2-(CH_2)_2-CO-NH-C\ (Me)_2-CH_2-OPO_3^{2-}$ w) from $Me_3SiO_{1/2}-$, $Me_2SiO-$, $-OMeSi\ (CH_2)_3N^+Hcycl.Hex-(CH_2)_2-CONHC\ (Me)_2CH_2OPO_3^{2-}$ x) from $Me_2SiO-$, $-_{1/2}OMe_2Si\ (CH_2)_3N^+Hcycl.Hex-(CH_2)_2-CONHC\ (Me_2)CH_2OPO_3^{2-}$ y) from $Me_3SiO_{1/2}-$, $Me_2SiO-$, $-OMeSi\ (CH_2)_3N^+HMe-(CH_2)_2-CONHC\ (Me)_2CH_2OPO_3^{2-}$ z) from $Me_2SiO-$, $-_{1/2}OMe_2Si\ (CH_2)_3N^+HMe-(CH_2)_2-CONHC\ (Me)_2CH_2OPO_3^{2-}$ 1) from $Me_3SiO_{1/2}-$, $Me_2SiO-$, $-OMeSi\ (CH_2)_3-N^+H_2-(CH_2)_2-CO-NH-CH_2-CH_2-OPO_3^{2-}$ 2) from $Me_2SiO-$, $-_{1/2}OMe_2Si\ (CH_2)_3-N^+H_2-(CH_2)_2-CO-NH-CH_2-CH_2-OPO_3^{2-}$ 3) from $Me_3SiO_{1/2}-$, $Me_2SiO-$, $-OMeSi\ (CH_2)_3N^+Hcycl.Hex-(CH_2)_2-CONHCH_2CH_2OPO_3^{2-}$ 4) from $Me_2SiO-$, $-_{1/2}OMe_2Si\ (CH_2)_3N^+Hcycl.Hex-(CH_2)_2-CONHCH_2CH_2OPO_3^{2-}$ 5) from $Me_3SiO_{1/2}-Me_2SiO-$, $-OMeSi\ (CH_2)_3N^+HMe-(CH_2)_2-CONHCH_2CH_2OPO_3^{2-}$ 6) from $Me_2SiO-$, $-_{1/2}OMe_2Si\ (CH_2)_3N^+HMe-(CH_2)_2-CONHCH_2CH_2OPO_3^{2-}$ 7) from $Me_3SiO_{1/2}-$, $Me_2SiO-$, $-OMeSi\ (CH_2)_3N^+H_2-(CH_2)_2-COOCH_2CH_2OOC-o-C_6H_4-COO^-$ 8) from $Me_2SiO-$, $-_{1/2}OMe_2Si\ (CH_2)_3N^+H_2-(CH_2)_2-COOCH_2CH_2OOC-o-C_6H_4-COO^-$ 9) from $Me_3SiO_{1/2}-$, $Me_2SiO-$, $-OMeSi\ (CH_2)_3N^+H_2-(CH_2)_2-COOCH_2CH\ (Me)\ OOC-o-C_6H_4-COO^-$ 10) from $Me_2SiO-$, $-_{1/2}OMe_2Si\ (CH_2)_3N^+H_2-(CH_2)_2-COOCH_2CH(Me)\ OOC-o-C_6H_4-COO^-$ 11) from $Me_3SiO_{1/2}-$, $Me_2SiO-$, $-OMeSi\ (CH_2)_3-NHCO-(CH_2)_2-N^+H_2-(CH_2)_2-SO_3^-$ 12) from $Me_2SiO-$, $-_{1/2}OMe_2Si\ (CH_2)_3-NHCO-(CH_2)_2-N^+H_2-(CH_2)_2-SO_3^-$ 13) from $Me_3SiO_{1/2}-$, $Me_2SiO-$, $-OMeSi\ (CH_2)_3-NHCO-(CH_2)_2-N^{30}H_2-(CH_2)_2-COO^{31}$ 14) from $Me_2SiO-$, $-_{1/2}OMe_2Si\ (CH_2)_3-NHCO-(CH_2)_2-N^+H_2-(CH_2)_2-COO^-$ 15) from $Me_3SiO_{1/2}-$, $Me_2SiO-$, $-OMeSi\ (CH_2)_3-N^+H_2-(CH_2)_2-CO-NH-C\ (Me)_2-CH_2-SO_3^--OMeSi\ (CH_2)_3-N^+H_3$, $-OMeSi\ (CH_2)_3-NH-(CH_2)_2-CO-NH-C\ (Me)_2-CH_2-SO_3^-$ 16) from $Me_2SiO-$, $-_{1/2}OMe_2Si\ (CH_2)_3-N^+H_2-(CH_2)_2-CO-NH-C\ (Me)_2-CH_2-SO_3^--OMeSi\ (CH_2)_3-N^+H_3$, $-_{1/2}OMe_2Si\ (CH_2)_3-NH-(CH_2)_2-CO-NH-C(Me)_2-CH_2-SO_3^-$ 17) from $Me_3SiO_{1/2}-$, $Me_2SiO-$, $-OMeSi\ (CH_2)_3N^+Hcycl.Hex-(CH_2)_2-CONHC(Me)_2CH_2SO_3^--OMeSi\ (CH_2)_3Ncycl.Hex-(CH_2)_2-CONHC\ (Me)_2CH_2SO_3^--OMeSi\ (CH_2)_3NH^{30}cycl.hexyl$ 18) from $Me_3SiO_{1/2}-$, $Me_2SiO-$, $-OMeSi\ (CH_2)_3N^+H_2-(CH_2)_2-COOCH_2CH_2OOCCH_2CH_2-COO^--OMeSi\ (CH_2)_3NH-(CH_2)_2-COOCH_2CH_2OOCCH_2CH_2-COO^--OMeSi\ (CH_2)_3NH_3^+$ 19) from $Me_3SiO_{1/2}-$, $Me_2SiO-$, $-OMeSi\ (CH_2)_3-N^+H_2-(CH_2)_2-CO-NH-C(Me)_2-CH_2-OPO_3^{2-}-OMeSi\ (CH_2)_3-NH-(CH_2)_2-CO-NH-C(Me)_2-CH_2-OPO_3^{2-}-OMeSi\ (CH_2)_3-NH_3^+$ 20) from $Me_3SiO_{1/2}-$, $Me_2SiO-$, $-OMeSi\ (CH_2)_3N^+H_2-(CH_2)_2-COOCH_2CH_2OOC-o-C_6H_4-COO^--OMeSi\ (CH_2)_3NH-(CH_2)_2-COOCH_2CH_2OOC-o-C_6H_4-COO^--OMeSi\ (CH_2)_3NH_3^+$ 21) from $Me_3SiO_{1/2}-$, $Me_2SiO-$, $-OMeSi\ (CH_2)_3N^+H_2-(CH_2)_2-COOCH_2CH(Me)\ OOC-o-C_6H_4-COO^-$ $-OMeSi\ (CH_2)_3NH-(CH_2)_2-COOCH_2CH\ (Me)\ OOC-o-C_6H_4-COO^--OMeSi\ (CH_2)_3NH_3^+$ 22) from $Me_3SiO_{1/2}-$, $Me_2SiO-$, $-OMeSi\ (CH_2)_3-NHCO-(CH_2)_2-N^+H_2\ (CH_2)_2-SO_3^-$ $-OMeSi\ (CH_2)_3-NHCO-(CH_2)_2-NH-(CH_2)_2-SO_3^-$, $-OMeSi\ (CH_2)_3NH_3^+$ and 23) from $Me_3SiO_{1/2}-$, $Me_2SiO-$, $-OMeSi(CH_2)_3N^+H_2-(CH_2)_2-NH-(CH_2)_2-COOCH_2CH\ (Me)\ OOC-o-C_6H_4-COO^-$ $-OMeSi(CH_2)_3NH-(CH_2)_2-NH-(CH_2)_2-COOCH_2CH\ (Me)\ OOC-o-C_6H_4-COO^-$ $-OMeSi(CH_2)_3NH_3^+$, where Me is the methyl radical and cycl.Hex is the cyclohexyl radical.

The ionic organosilicon compounds according to the invention have an average molecular weight $M_n$ of preferably 500 to 1,000,000 g/mole, more preferably 1,000 to 150,000 g/mole.

The ionic organosilicon compounds according to the invention have a viscosity of preferably 10 to 1,000,000 $mm^2/s$, more preferably 20 to 100,000 $mm^2/s$, in each case at 25° C.

The ionic organosilicon compounds according to the invention are preferably those which are made up a) from $Me_3SiO_{1/2}$—, $Me_2SiO$—, —$OMeSi(CH_2)_3$—$N^+H_2$—$(CH_2)_2$—CO—NH—C$(Me)_2$—$CH_2$—$SO_3^-$ b) from $Me_2SiO$—, —$_{1/2}OMe_2Si(CH_2)_3$—$N^+H_2$—$(CH_2)_2$—CO—NH—C$(Me)_2$—$CH_2$—$SO_3^-$ c) from $Me_3SiO_{1/2}$—, $Me_2SiO$—, —$OMeSi(CH_2)_3N^+$Hcycl.Hex—$(CH_2)_2$—CONHC$(Me)_2CH_2SO_3^-$ d) from $Me_2SiO$—, —$_{1/2}OMe_2Si(CH_2)_3N^+$Hcycl.Hex—$(CH_2)_2$—CONHC$(Me)_2CH_2SO_3^-$ e) from $Me_3SiO_{1/2}$—, $Me_2SiO$—, —$OMeSi(CH_2)_3N^+$HMe—$(CH_2)_2$—CONHC$(Me)_2CH_2SO_3^-$ f) from $Me_3SiO_{1/2}$—, $Me_2SiO$—, —$OMeSi(CH_2)_3$NH$_2$—$(CH_2)_2$—$COOCH_2CH_2OOCCH_2CH_2$—$COO^-$ g) from $Me_2SiO$—, —$_{1/2}OMe_2Si(CH_2)_3N^+H_2$—$(CH_2)_2$—$COOCH_2CH_2OOCCH_2CH_2$—$COO^-$ h) from $Me_3SiO_{1/2}$—, $Me_2SiO$—, —$OMeSi(CH_2)_3N^+$HMe—$(CH_2)_2$—$COOCH_2CH_2OOCCH_2CH_2$—$COO^-$ i) from $Me_2SiO$—, —$_{1/2}OMe_2Si(CH_2)_3N^+$HMe—$(CH_2)_2$—$COOCH_2CH_2OOCCH_2CH_2$—$COO^-$ j) from $Me_3SiO_{1/2}$—, $Me_2SiO$—, —$OMeSi(CH_2)_3$—$N^+H_2$—$(CH_2)_2$—CO—NH—$CH_2$—$CH_2$—$OPO_3^{2-}$ k) from $Me_2SiO$—, —$_{1/2}OMe_2Si(CH_2)_3$—$N^+H_2$—$(CH_2)_2$—CO—NH—$CH_2$—$CH_2$—$OPO_3^{2-}$ l) from $Me_3SiO_{1/2}$—, $Me_2SiO$—, —$OMeSi(CH_2)_3N^+H_2$—$(CH_2)_2$—$COOCH_2CH_2OOC$-o-$C_6H_4$—$COO^-$ m) from $Me_2SiO$—, —$_{1/2}OMe_2Si(CH_2)_3N^+H_2$—$(CH_2)_2$—$COOCH_2CH_2OOC$-o-$C_6H_4$—$COO^-$ n) from $Me_3SiO_{1/2}$—, $Me_2SiO$—, —$OMeSi(CH_2)_3N^+H_2$—$(CH_2)_2$—$COOCH_2CH(Me)OOC$-o-$C_6H_4$—$COO^-$ o) from $Me_2SiO$—, —$_{1/2}OMe_2Si(CH_2)_3N^+H_2$—$(CH_2)_2$—$COOCH_2CH(Me)OOC$-o-$C_6H_4$—$COO^-$ p) from $Me_3SiO_{1/2}$, $Me_2SiO$—, —$OMeSi(CH_2)_3$—NHCO—$(CH_2)_2$—$N^+H_2$—$(CH_2)_2$—$COO^-$ q) from $Me_2SiO$—, —$_{1/2}OMe2Si(CH_2)_3$—NHCO—$(CH_2)_2$—$N^+H_2$—$(CH_2)_2$—$COO^-$ r) from $Me_3SiO_{1/2}$—, $Me_2SiO$—, —$OMeSi(CH_2)_3$—$N^+H_2$—$(CH_2)_2$—CO—NH—C$(Me)_2$—$CH_2$—$SO_3^-$ —$OMeSi(CH_2)_3$—$N^+H^+H_3$, —$OMeSi(CH_2)_3$—NH—$(CH_2)_2$—CO—NH—C$(Me)_2$—$CH_2$—$SO_3^-$ s) from $Me_2SiO$—, —$_{1/2}OMe_2Si(CH_2)_3$—$N^+H_2$—$(CH_2)_2$—CO—NH—C$(Me)_2$—$CH_2$—$SO_3^-$—$OMeSi(CH_2)_3$—$N^+H_3$ —$_{1/2}OMe_2Si(CH_2)_3$—NH—$(CH_2)_2$—CO—NH—C$(Me)_2$—$CH_2$—$SO_3^-$ t) from $Me_3SiO_{1/2}$—, $Me_2SiO$—, —$OMeSi(CH_2)_3N^+H_2$—$(CH_2)_2$—$COOCH_2CH_2OOCCH_2CH_2$—$COO^-$—$OMeSi(CH_2)_3NH$—$(CH_2)_2$—$COOCH_2CH_2OOCCH_2CH_2$—$COO^-$—$OMeSi(CH_2)_3NH_3^+$ u) from $Me_3SiO_{1/2}$—, $Me_2SiO$—, —$OMeSi(CH_2)_3$—$N^+H_2$—$(CH_2)_2$—CO—NH—C$(Me)_2$—$CH_2$—$OPO_3^{2-}$ —$OMeSi(CH_2)_3$—NH—$(CH_2)_2$—CO—NH—C$(Me)_2$ —$CH_2$—$OPO_3^{2-}$ —$OMeSi(CH_2)_3$—$NH_3^+$ v) from $Me_3SiO_{1/2}$—, $Me_2SiO$—, —$OMeSi(CH_2)_3N^+H_2$—$(CH_2)_2$—$COOCH_2CH_2OOC$-o-$C_6H_4$—$COO^-$ —$OMeSi(CH_2)_3NH$—$(CH2)_2$—$COOCH_2CH_2OOC$-o-$C_6H_4$—$COO^-$ —$OMeSi(CH_2)_3NH_3^+$ w) from $Me_3SiO_{1/2}$—, $Me_2SiO$—, —$OMeSi(CH_2)_3N^+H_2$ —$(CH_2)_2$—$COOCH_2CH(Me)OOC$-o-$C_6H_4$—$COO^-$ —$OMeSi(CH_2)_3NH$—$(CH_2)_2$—$COOCH_2CH(ME)OOC$-o-$C_5H_4$—$COO^-$ —$OMeSi(CH_2)_3NH_3^+$ and x) from $Me_3SiO_{1/2}$—, $Me_2SiO$—, —$OMeSi(CH_2)_3N^+H_2$—$(CH_2)_2$—NH—$(CH_2)_2$—$COOCH_2CH(Me)OOC$-o-$C_6H_4$—$COO^-$ —$OMeSi(CH_2)_3NH$—$(CH_2)_2$—NH—$(CH_2)_2$—$COOCH_2CH(Me)OOC$-o-$C_6H_4$—$COO^-$ —$OMeSi(CH_2)_3NH_3^+$, where Me is the methyl radical and cycl.Hex is the cyclohexyl radical The ionic organosilicon compounds according to the invention are preferably those which are made up a) from $Me_3SiO_{1/2}$—, $Me_2SiO$—, —$OMeSi(CH_2)_3$—$N^+H_2$—$(CH_2)_2$—CO—NH—C$(Me)_2$—$CH_2$—$SO_3^-$p1 b) from $Me_2SiO$—, —$_{1/2}OMe_2Si(CH_2)_3$—$N^+H_2$—$(CH_2)_2$—CO—NH—C$(Me)_2$—$CH_2$—$SO_3^-$ c) from $Me_3SiO_{1/2}$—, $Me_2SiO$—, —$OMeSi(CH_2)_3N^+H_2$—$(CH_2)_2$—$COOCH_2CH_2$—$OOCCH_2CH_2$—$COO^-$ d) from $Me_2SiO$—, —$_{1/2}OMe_2Si(CH_2)_3N^+H_2$—$(CH_2)_2$—$COOCH_2CH_2OOCCH_2CH_2$—$COO^-$ e) from $Me_3SiO_{1/2}$—, $Me_2SiO$—, —$OMeSi(CH_2)_3N^+H_2$—$(CH_2)_2$—$COOCH_2CH_2OOC$-o-$C_6H_4$—$COO^-$ f) from $Me_2SiO$—, —$_{1/2}OMe_2Si(CH_2)_3N^+H_2$—$(CH_2)_2$—$COOCH_2CH_2OOC$-o-$C_6H_4$—$COO^-$ g) from $Me_3SiO_{1/2}$—, $Me_2SiO$—, —$OMeSi(CH_2)_3$—$N^+H_2$—$(CH_2)_2$—CO—NH—C$(Me)_2$—$CH_2$—$SO_3^-$ —$OMeSi(CH_2)_3$—$N^+H_3$, —$OMeSi(CH_2)_3$—NH—$(CH_2)_2$—CO—NH—C$(Me)_2$—$CH_2$—$SO_3^-$ h) from MeSiO—, —$_{1/2}OMe_2Si(CH_2)_3$—$N^+H_2$—$(CH_2)_2$—CO—NH—C$(Me)_2$ —$CH_2$—$SO_3^-$ —$OMeSi(CH_2)_3$ $N^+H_3$ —$_{1/2}OMe_2Si(CH_2)_3$—NH—$(CH_2)_2$—CO—NH—C$(Me)_2$—$CH_2$—$SO_3^-$ i) from $Me_3SiO_{1/2}$—, $Me_2SiO$—, —$OMeSi(CH_2)_3N^+H_2$—$(CH_2)_2$—$COOCH_2CH2OOCCH_2$—$CH_2$—$COO^-$, —$OMeSi(CH_2)_3NH$—$(CH_2)_2$—$COOCH_2CH_2OOCCH_2CH_2$—$COO^-$, —$OMeSi(CH_2)_3$ $NH_3^+$ j) from $Me_3SiO_{1/2}$—, $Me_2SiO$—, —$OMeSi(CH_2)_3N^+H_2$—$(CH_2)_2$—$COOCH_2CH_2OOC$-o-$C_6H_4$—$COO^-$ —$OMeSi(CH_2)_3NH$—$(CH_2)_2$-$COOCH_2CH_2OOC$-o-$COO^-$, —$OMeSi(CH_2)_3NH_3^+$ k) from $Me_3SiO_{1/2}$—, $Me_2SiO$—, —$OMeSi(CH_2)_3N^+H_2$—$(CH_2)_2$—$COOCH_2CH(Me)OOC$-o-$C_6H_4$—$COO^-$ —$OMeSi(CH_2)_3NH$—$(CH_2)_2$—$COOCH_2CH(Me)OOC$-o-$C_6H_4$—$COO^-$, —$OMeSi(CH_2)_3NH_3^+$ and l) from $Me_3SiO$—, $Me_2SiO$—, —$OMeSi(CH_2)_3N^+H_2$—$(CH_2)_2$—NH—$(CH_2)_2$—$COOCH_2CH(Me)OOC$-o-$C_6H_4$-$COO^-$ —$OMeSi(CH_2)_3$—$(CH_2)_2$—NH—$(CH_2)_2$ -$COOCH_2CH(Me)OOC$-o-$C_6H_4$—COO—, —$OMeSi(CH_2)_3NH_3^+$, where Me is the methyl radical and the lower case o in -o-$C_6H_4$ indicates the group to its left is in the ortho position.

The invention further relates to a process for the preparation of ionic organosilicon compounds, which comprises reacting organosilicon compounds comprising units of the formula $$R_gX_cSiO_{(4-g-c)/2} \tag{VIII}$$

in which R, X and c have the meanings given above and g is 0, 1, 2 or 3, with the proviso that the sum is g+c  4 and the organosilicon compounds contain at least one radical R of the formula (II), (III) or (IV) per molecule, with compounds chosen from those of the formulae

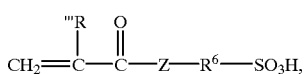
(IX)

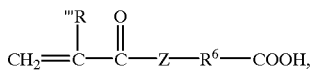
(X)

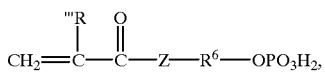
(XI)

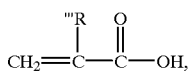
(XII)

if the organosilicon compound used contains at least one radical R of the formula (II) or (III), or with compounds chosen from those of the formulae $$R'''NH—R^5—SO_3H \tag{XIII}$$

and $$R'''NH—R^5—COOH \tag{XIV},$$

if the organosilicon compound used contains at least one radical R of formula (IV),
in which
$R^5, R^6, R'''$ and Z in each case can be identical or different and have one of the meanings given above for these radicals.

The reaction according to the invention can be carried out in bulk, solution or emulsion. The components used can be mixed with one another in any desired manner known.

The organosilicon compounds used in the process according to the invention are preferably those which consist of units of formula (VIII).

The organosilicon compounds which are used according to the invention and comprise units of formula (VIII) can be any desired organosilicon compounds, such as, organosilanes, as well as linear, branched and cyclic organosiloxanes, siloxanes being preferred.

The organosilicon compounds which are used in the process according to the invention and have a radical of formula (II) having an amine number (ml of 1 N HCl consumed for 1 g of substance) of at least 0.003, preferably 0.01 to 6. If the radical R in the units of formula (VIII) corresponds to formula (III), the organosilicon compounds used according to the invention preferably have a mercapto content of 0.1% to 40% by weight. If the radical R in the units of formula (VIII) corresponds to formula (IV), the organosilicon compounds used according to the invention preferably have an acrylic content ($H_2C=CR'''C(O)Z—$) of 0.1% to 40% by weight.

The organosilicon compounds used according to the invention have an average viscosity of 5 to 20,000 mm$^2$/s, preferably 10 to 5000 mm$^2$/s, more preferably 10 to 2000 mm$^2$/s, in each case at 25° C.

Organosilicon compounds comprising units of formula (VIII) which are used in the process according to the invention are preferably those of the formula $$R_3SiO(SiR_2O)_rSiR_3 \tag{XV}$$

in which
R is identical or different and have the meaning given above for this radical and r is 0 or an integer from 1 to 1500, preferably 1 to 500, with the proviso that in formula (XV) at least one R corresponds to a radical of the formula (II),(III) or (IV).

Examples of the organosilicon compounds used in the process according to the invention are a) α,ω-trimethyl-silyl-terminated dimethyl-/methylaminopropylsiloxane, α,ω-dimethyl-aminopropyl-silyl-terminated dimethylsiloxane, α,ω-dimethyl-aminopropyl-silyl-terminated dimethyl-/methyl-amino-propyl-siloxane having an amine number of 0.003 to 6, b) α,ω-trimethylsilyl-terminated dimethyl-/methylaminoethylaminopropyl-siloxane, α,ω-dimethylaminoethyl-aminopropyl-silyl-terminated dimethylsiloxane, α,ω-dimethyl-aminoethylaminopropyl-silyl-terminated dimethyl-/methyl-aminoethylaminopropyl-siloxane having an amine number of 0.003 to 12, c) α,ω-trimethylsilyl-terminated dimethyl-/methyl-, N,N-diethylaminoethylamino-propyl-siloxane, α,ω-dimethyl-, N,N-diethylaminoethylaminopropyl-silyl-terminated dimethylsiloxane, α, ω-dimethyl-, N,N-diethylaminoethylaminopropyl-silyl-terminated dimethyl/methyl-, N,N-diethylaminoethylaminopropyl-siloxane having an amine number of 0.003 to 12, d) α,ω-trimethylsilyl-terminated dimethyl-/methyl-, N,N-dimethylaminopropylamino-propyl-siloxane, α, ω-dimethyl-, N,N-dimethylaminopropylaminopropyl-silyl-terminated dimethylsiloxane, α, ω-dimethyl-, N,N-dimethylaminopropylaminopropyl-silyl-terminated dimethyl-/methyl-, N,N-dimethylaminopropylamino-propyl-siloxane having an amine number of 0.003 to 12, e) α,ω-trimethylsilyl-terminated dimethyl-/methyl-, N-cyclohexylaminopropyl-siloxane, α, ω-dimethyl-, N-cyclohexylaminopropyl-silyl-terminated dimethylsiloxane, α, ω-dimethyl-N-cyclo-hexylaminopropyl-silyl-terminated dimethyl-/methyl-, N-cyclohexyl-aminopropyl-siloxane having an amine number of 0.003 to 12, f) α,ω-trimethylsilyl-terminated dimethyl-/methyl-mercaptopropyl-siloxane, α, ω-dimethyl-mercaptopropyl-silyl-terminated dimethylsiloxane, α, ω-dimethyl-mercaptopropyl-silyl-terminated dimethyl-/methyl-mercaptopropyl-siloxane having a mercapto content (% by weight of SH) of 0.1% to 40% and g) α,ω-trimethylsilyl-terminated dimethyl-/methyl-acrylamidopropyl-siloxane, α, ω-dimethylacrylamidopropyl-silyl-terminated dimethylsiloxane, α, ω-dimethyl-acrylamidopropyl-silyl-terminated dimethyl-/methyl-acrylamidopropyl-siloxane having an acrylamido content (% by weight of $H_2C=CHCONH—$) of 0.1% to 40%.

Examples of the compounds of formulae (IX) to (XIV) used according to the invention are 2-acrylamido-2-methylpropanesulfonic acid, 2-acrylamido-propanesulfonic acid, acrylamido-propane-sulfonic acid, 2-acryl(N-methyl)-amido-2-methylpropanesulfonic acid, 2-acrylamido-2-methylpropanecarboxylic acid, 2-acrylamido-propanecarboxylic acid, acrylamidopropanecarboxylic acid, 2-acryl(N-methyl)amido-2-methylpropanecarboxylic acid, 2-acryloyloxyethyl hydrogen phthalate, 2-acryloyloxypropyl hydrogen phthalate, B-acryloyloxyethyl hydrogen succinate, 2-acrylamido-2- methylpropane dihydrogen phosphate, taurine, 3-aminopropanesulfonic acid, 2-aminoethanecarboxylic acid, 3-amino-propanecarboxylic acid, acryloyl dihydrogen phosphate, acrylic acid and methacrylic acid.

The compounds of formula (IX) to (XIV) used according to the invention are preferably 2-acrylamido-2-methylpropanesulfonic acid, 2-acrylamido-propanesulfonic acid, 2-acryloyloxyethyl hydrogen phthalate, 2-acryloyloxypropyl hydrogen phthalate β-acryloyloxyethyl hydrogen succinate, where 2-acrylamido-2-methylpropanesulfonic acid, 2-acryloyloxyethyl hydrogen phthalate, 2-acryloyloxypropyl hydrogen phthalate, and β-acryloyloxyethyl hydrogen succinate are preferred.

The organosilicon compounds used according to the invention which comprise units of formula (VIII) and the compounds of formulae (IX) to (XIV) are commercially available products or can be prepared by methods known in chemistry.

In the process according to the invention, the acrylate-containing compounds of formulae (IX) to (XII) used according to the invention are preferably present in amounts of 0.001 to 5 mole, more preferably 0.01 to 2 mole, per mole of amine/mercapto function according to formula (II) or (III) in the organosilicom compound, in particular 0.1 to 0.5 mole of compounds of formulae (IX) to (XII) per mole of amine/mercapto function according to formula (II), and 0.1 to 1.0 mole of compounds of formulae (IX) to (XII) per mole of amine/mercapto function according to formula (III).

In the process according to the invention, the amino acid-containing compounds of formulae (XIII) and (XIV) used according to the invention are preferably present in amounts of 0.001 to 5 mole, more preferably 0.01 to 2 mole, in particular 0.1 to 1.0 mole, per mole of acrylic function according to formula (IV) in the organosilicon compound.

All the known compounds which catalyze reactions similar to Michael additions can be used in the process according to the invention, such as, metal compounds from the group consisting of Lewis acids, organic or inorganic acids and bases, which is not preferred. Examples of such catalysts are compounds of tin, such as, tin(IV) chloride, or of aluminum, such as aluminum(III) chloride, acetic acid, hydrochloric acid, sulfuric acid, nitric acid, alkali metal or alkaline earth metal hydroxides or amines, such as, triethylamine.

If a catalyst is used in the process according to the invention, the amounts are preferably 0.01% to 10% by weight, more preferably 0.1% to 5% by weight, in each case based on the total weight of the reactive components.

Substances which prevent polymerization, so-called inhibitors, can be used in the process according to the invention. The inhibitors can be any desired inhibitors which have been used to date for suppressing the polymerization of acrylates, such as, hydroquinone monomethyl ether, benzothiazine, diphenylpicrylhydrazyl, phenols or sulfur compounds.

If inhibitors are used in the process according to the invention, the amounts are preferably 0.000001% to 1% by weight, more preferably 0.0001% to 0.1% by weight, in each case based on the total weight of the reactive components.

Organic solvents which are inert toward the reactive components can be co-used in the process according to the invention. Examples of organic solvents which are used optionally are methanol, ethanol, toluene, xylene, tetrahydrofuran, n-butyl acetate, isopropanol, isophorone, octane isomers and acetonitrile. If solvents are used they are preferably methanol, n-butyl acetate, toluene and isopropanol. If solvents are used, the amounts are preferably 1% to 50% by weight, based on the total weight of the reactive components.

The components used in the process according to the invention can in each case be one type of such a component or a mixture of at least two types of a particular component.

In a preferred embodiment of the process according to the invention, organosilicon compounds of units of formula (VIII) with radicals R of formula (II) or (IV) are reacted with at least one compound of formula (IX), (X) or (XI), or (XIII).

In a preferred embodiment of the process according to the invention, organosilicon compounds of units of formula (VIII) with radicals R of formula (II) are reacted with at least one compound of formula (IX) or (X).

The process according to the invention is carried out under the pressure of the ambient atmosphere, at between 900 and 1100 hPa, but it can also be carried out under higher or lower pressures. The process according to the invention is preferably carried out at a temperature of 0° to 150° C., more preferably 20° to 100° C.

Excess organic compound of formulae (IX) to (XIV) is removed from the ionic organosilicon compounds prepared by the process according to the invention by extraction, and any inert organic solvent co-used is preferably removed from these compounds by distillation.

The process according to the invention has the advantage that it is easy to carry out and a high, complete, conversion is achieved.

The process according to the invention also has the advantage that the organosilicon compounds to be used can be reacted at relatively low temperatures, preferably 20° to 60° C., in short reaction times and without discoloration to give clear products, and the viscosity can be adjusted in a controlled manner via the extent of the deficit of organic compound used.

The process according to the invention furthermore has the advantage that the ionic organosilicon compounds can be prepared with a high selectivity and using educts which are as a rule readily accessible.

Optionally, the ionic organosilicon compounds obtained by the process according to the invention can be equilibrated with organopolysiloxanes (1), preferably chosen from the group consisting of linear organopolysiloxanes containing terminal triorganosiloxy groups, linear organopolysiloxanes containing terminal hydroxyl groups, cyclic organopolysiloxanes and copolymers of diorganosiloxane and monoorganosiloxane units, as a result it becomes possible to establish the desired molecular weight, and to distribute the ionic groups in the molecule in a controlled manner.

In the context of the present invention, the term organopolysiloxanes is intended to mean polymeric, oligomeric and dimeric siloxanes.

Preferably, linear organopolysiloxanes containing terminal triorganosiloxy groups which are used are those of the formula $$R^7{}_3SiO\,(SiR^7{}_2O)_u SiR^7{}_3 \qquad (XVI),$$

linear organopolysiloxanes containing terminal hydroxyl groups which are used are those of the formula $$HO(SiR^7{}_2O)_v H \qquad (XVII),$$

cyclic organopolysiloxanes which are used are those of the formula $$(SiR^7{}_2O)_w \qquad (XVIII)$$

and copolymers which are used are those comprising units of the formulae $$R^7{}_3SiO_{1/2},\ R^7{}_2SiO\ \text{and}\ R^7SiO_{3/2}$$

in which

R[7] is identical or different and is optionally halogented hydrocarbon radicals having 1 to 12 carbon atoms, u is 0 or an integer having a value from 1 to 1500, v is 0 or an integer having a value from 1 to 1500 and w is an integer having a value from 3 to 12.

Examples of radicals R[7] are the examples given above for R as optionally halogenated hydrocarbon radicals, R[7] as an alkyl radical having 1 to 12 carbon atoms being preferred.

The ratios of the amounts of the organopolysiloxanes (1) used in the equilibration carried out optionally and the ionic organosilicon compounds prepared according to the invention are determined only by the desired proportion of ionic groups in the organopolysiloxanes produced in the equilibration carried out, optionally, and by the desired average chain length.

In the equilibration which is carried out, optionally, acid or basic catalysts which promote the equilibration are used, basic catalysts being preferred.

Examples of acid catalysts are sulfuric acid, phosphoric acid, trifluoromethanesulfonic acid, phosphonitrile chlorides and acid catalysts which are solid under the reaction conditions, such as acid-activated fuller's earth, acid zeolites, sulfonated charcoal and sulfonated styrene/divinylbenzene copolymers, phosphonitrile chlorides being preferred as acid catalysts. Acid catalysts are preferably used in amounts of 5 to 1000 ppm (=parts per million) by weight, in particular 50 to 200 ppm by weight, in each case based on the total weight of the organosilicon compounds used.

Examples of basic catalysts are benzyltrimethylammonium hydroxide, tetramethylammonium hydroxide, alkali metal hydroxide and alkaline earth metal hydroxide in methanolic solution and silanolates.

Alkali metal hydroxides are preferred, and are used in amounts of 50 to 10000 ppm (parts per million) by weight, in particular 500 to 2000 ppm, in each case based on the total weight of the organosilicon compounds used.

The equilibration which is carried out, optionally, is carried out at 80° C. to 150° C. under the pressure of the ambient atmosphere, at between about 900 and 1100 hPa. However, it can be carried out under higher or lower pressures.

Optionally, the equilibration can be carried out in a water-immiscible solvent, such as toluene, but this is not preferred. If such organic solvents are used, amounts of 5% to 20% by weight, based on the total weight of the organosilicon compounds used, are preferred.

Before working up the mixture obtained in the equilibration, the catalyst can be rendered inactive.

The ionic organosilicon compounds according to the invention and prepared according to the invention have the advantage that they are odorless and, water-clear.

The ionic organosilicon compounds according to the invention and prepared according to the invention furthermore have the advantage that in the form of an emulsion, when used in textile finishing, in addition to good hydrophilic properties and good antistatic properties, they lead to an excellent, fluffy soft handle.

The ionic organosilicon compounds according to the invention and prepared according to the invention have the advantage that they have a complexing action on transition metals and thus, permanently bond these in leather finishing (chrome-tanned), and lead to a permanent hydrophilic finish with the desired soft handle.

The ionic organosilicon compounds according to the invention and prepared according to the invention can be used for all purposes for which organosilicon compounds, in particular organosilicon compounds containing amino groups, have been used to date. The ionic organosilicon compounds according to the invention are suitable for the treatment of organic fibers, such as fiber lubricants and spinning preparations, as well as for formulations in the polish sector.

In the following examples, all parts and percentages of data are based on the weight, unless stated otherwise. Unless stated otherwise, the following examples are carried out under a pressure of the ambient atmosphere, at about 1000 hPa, and at room temperature, about 20° C., or a temperature which is established when the reactants are brought together at room temperature without additional heating or cooling. All the viscosity data stated in the examples are intended to relate to a temperature of 25° C.

In the examples, the figure which indicates the amount of iodine consumed, during addition to the aliphatic multiple bond, in grams per 100 grams of material to be analyzed is called the iodine number.

EXAMPLE 1

20 g of an α,ω-aminopropyl-dimethyl-terminated polydimethylsiloxane having an amine number of 0.436 and a viscosity of 93 mm$^2$/s are dissolved in 20 g of isopropanol and the solution is heated to 70° C. 0.9 g (4.3 mmol) of 2-acrylamido-2-methyl-1-propanesulfonic acid are dissolved in 9 g of methanol and the solution is added dropwise to the isopropanol/siloxane solution, heated at 70° C., in the course of 10 minutes. After a reaction time of a further 2 hours at 70° C., the mixture is cooled to room temperature. Finally, the solvents are stripped off to constant weight with the aid of a rotary evaporator at 50° C. under an oil pump vacuum. 20.8 g of a clear oil having a viscosity of 2784 mm$^2$/s are obtained.

EXAMPLE 2

20 g of an α,ω-aminopropyl-dimethyl-terminated polydimethylsiloxane having an amine number of 2.432 and a viscosity of 11.8 mm$^2$/s are dissolved in 20 g of isopropanol and the solution is heated to 70° C. 5 g of 2-acrylamido-2-methyl-1-propanesulfonic acid (0.024 mole) are dissolved in 50 g of methanol and the solution is added dropwise to the isopropanol/siloxane solution, heated at 70° C., in the course of 15 minutes. After a reaction time of a further 2 hours at 70° C., the mixture is cooled to room temperature. Finally, the solvents are stripped off to constant weight with the aid of a rotary evaporator at 50° C. under an oil pump vacuum. 25 g of a clear, yellowish oil having a viscosity of 34536 mm$^2$/s are obtained.

EXAMPLE 3

50 g of an α,ω-trimethyl-terminated dimethyl/methylaminopropyl-polysiloxane having an amine number of 0.081 and a viscosity of 270 mm$^2$/s are dissolved in 25 g of isopropanol and the solution is heated to 70° C. 0.42 g of 2-acrylamido-2-methyl-1-propanesulfonic acid (0.002 mole) is dissolved in 4.2 g of methanol and the solution is added dropwise to the isopropanol/siloxane solution, heated at 70° C., in the course of 10 minutes. After a reaction time of a further 2 hours at 70° C., the mixture is cooled to room temperature. Finally, the solvents are stripped off to constant weight with the aid of a rotary evaporator at 50° C. under an oil pump vacuum. 49.4 g of a clear oil having a viscosity of 663 mm$^2$/s are obtained.

EXAMPLE 4

20 g of an α,ω-methoxy-dimethyl-terminated dimethyl-/methyl-aminopropyl-polysiloxane having an amine number of 0.292 and a viscosity of 1002 mm$^2$/s, 0.6 g of 2-acrylamido-2-methyl-1-propanesulfonic acid (2.92 mmol) and 0.412 g of 1% strength hydroquinone monomethyl ether solulution in isopropanol (200 ppm of inhibitor) are dissolved in 20 g of isopropanol and the solution is heated to 70° C. After a reaction time of 2 hours at 70° C., the mixture is cooled to room temperature. Finally, the solvent is stripped off to constant weight with the aid of a rotary evaporator at 50° C. under an oil pump vacuum. 20.9 g of a clear, slightly yellowish oil having a viscosity of 50423 mm$^2$/s are obtained.

EXAMPLE 5

20 g of an α,ω-trimethyl-terminated dimethyl/methylaminopropyl-polysiloxane having an amine number of 0.249 and a viscosity of 207 mm$^2$/s, 0.52 g of 2-acrylamido-2-methyl-1-propanesulfonic acid (2.5 mmol) and 0.41 g of 1% strength hydroquinone monomethyl ether solution in isopropanol (200 ppm of inhibitor) are dissolved in 20 g of isopropanol and the solution is heated to 70° C. After a reaction time of 2 hours at 70° C., the mixture is cooled to room temperature. Finally, the solvent is stripped off to constant weight with the aid of a rotary evaporator at 50° C. under an oil pump vacuum. 20.0 g of a clear oil having a viscosity of 12474 mm$^2$/s are obtained.

EXAMPLE 6

20 g of an α,ω-aminopropyl-dimethyl-terminated polydimethylsiloxane having an amine number of 0.436 and a viscosity of 93 mm$^2$/s and 0.9 g of 2-acrylamido-2-methyl-1-propanesulfonic acid (43 mmol) are dissolved in 20 g of isopropanol and the solution is heated to 70° C. After a reaction time of 2 hours at 70° C., the mixture is cooled to room temperature. Finally, the solvent is stripped off to constant weight with the aid of a rotary evaporator at 50° C. under an oil pump vacuum. 19.8 g of a clear oil having a viscosity of 2777 mm$^2$/s are obtained.

EXAMPLE 7

20 g of an α,ω-aminopropyl-dimethyl-terminated polydimethylsiloxane having an amine number of 2.432 and a viscosity of 11.8 mm$^2$/s and 5 g of 2-acrylamido-2-methyl-1-propanesulfonic acid (0.024 mmol) are dissolved in 20 g of isopropanol and the solution is heated to 70° C. After a reaction time of 2 hours at 70° C., the mixture is cooled to room temperature. Finally, the solvent is stripped off to constant weight with the aid of a rotary evaporator at 50° C. under an oil pump vacuum. 24.3 g of an oil having a viscosity of 34529 mm$^2$/s are obtained.

EXAMPLE 8

20 g of an α,ω-methoxy-dimethyl-terminated dimethyl-/methyl-aminopropyl-polysiloxane having an amine number of 0.292 and a viscosity of 1002 mm$^2$/s, 0.12 g of 2-acrylamido-2-methyl-1-propanesulfonic acid (0.58 mmol) and 0.40 g of 1% strength hydroquinone monomethyl ether solution in isopropanol (200 ppm of inhibitor) are dissolved in 20 g of isopropanol and the solution is heated to 70° C. After a reaction time of 2 hours at 70° C., the mixture is cooled to room temperature. Finally, the solvent is stripped off to constant weight with the aid of a rotary evaporator at 50° C under an oil pump vacuum. 19.4 g of a clear oil having a viscosity of 13093 mm2/s are obtained.

EXAMPLE 9

20 g of an α,ω-aminopropyl-dimethyl-terminated polydimethylsiloxane having an amine number of 0.436 and a viscosity of 93 mm$^2$/s are dissolved in 20 g of isopropanol and the solution is heated to 70° C. A solution of 1.21 g of 2-acryloyloxypropyl hydrogen phthalate (4.36 mmol) and 5 g of isopropanol is metered into this solution in the course of 5 minutes. After a reaction time of 2 hours at 70° C., the mixture is cooled to room temperature. Finally, the solvent is stripped off to constant weight with the aid of a rotary evaporator at 50° C. under an oil pump vacuum. 21.1 g of a clear oil having a viscosity of 2186 mm$^2$/s are obtained.

EXAMPLE 10

20 g of an α,ω-aminopropyl-dimethyl-terminated polydimethylsiloxane having an amine number of 0.436 and a viscosity of 93 mm$^2$/s are dissolved in 20 g of isopropanol and the solution is heated to 70° C. A solution of 0.94 g of B-acryloyloxyethyl hydrogen succinate (4.36 mmol) and 5 g of isopropanol is metered into this solution in the course of 5 minutes. After a reaction time of 2 hours at 70° C., the mixture is cooled to room temperature. Finally, the solvent is stripped off to constant weight with the aid of a rotary evaporator at 50° C. under an oil pump vacuum. 20.6 g of a clear oil having a viscosity of 3619 mm$^2$/s are obtained.

EXAMPLE 11

40 g of an α,ω-trimethyl-terminated dimethyl/methylaminopropyl-polysiloxane having an amine number of 0.249 and a viscosity of 207 mm$^2$/s are dissolved in 40 g of isopropanol and the solution is heated to 70° C. A solution of 1.08 g of B-acryloyloxyethyl hydrogen succinate (4.98 mmol) and 5 g of isopropanol is metered into this solution in the course of 5 minutes. After a reaction time of 2 hours at 70° C., the mixture is cooled to room temperature. Finally, the solvent is stripped off to constant weight with the aid of a rotary evaporator at 50° C. under an oil pump vacuum. 41.0 g of a clear oil having a viscosity of 5773 mm$^2$/s are obtained.

EXAMPLE 12

40 g of an α,ω-trimethyl-terminated dimethyl/methylmercaptopropyl-polysiloxane having a mercapto content of 0.51% (percent by weight) and a viscosity of 114 mm$^2$/s are dissolved in 40 g of isopropanol and the solution is heated to 70° C. 0.9 g (4.3 mmol) of 2-acrylamido-2-methyl-1-propanesulfonic acid are neutralized with 0.8 g (4.3 mmol) of dodecylamine in 9 g of methanol and the mixture is added dropwise to the isopropanol/siloxane solution, heated at 70° C., in the course of 10 minutes. After a reaction time of 2 hours, the mixture is cooled to room temperature. Finally, the solvent is stripped off to constant weight with the aid of a rotary evaporator at 50° C. under an oil pump vacuum. 41.0 g of a clear oil having a viscosity of 3216 mm$^2$/s are obtained.

EXAMPLE 13

100 g of an α,ω-dimethyl-acrylatoalkenyl-terminated dimethylpolysiloxane having an iodine number of 12 and a viscosity of 421 mm$^2$/s are dissolved in 50 g of tetrahydrofuran and the solution is heated to 60° C. 5.9 g (47.3 mmol) of taurine in 10 g of methanol are added dropwise to the tetrahydrofuran/siloxane solution, heated at 60° C., in the course of 15 minutes. After a reaction time of 2 hours, the mixture is cooled to room temperature. Finally, the solvents are stripped off to constant weight with the aid of a rotary evaporator at 50° C. under an oil pump vacuum. 103.9 g of a clear oil having a viscosity of 5174 mm$^2$/s are obtained.

EXAMPLE 14

20 g of an α,ω-aminopropyl-dimethyl-terminated polydimethylsiloxane having an amine number of 0.436 and a viscosity of 93 mm$^2$/s are heated to 70° C. 0.94 g of β-acryloyloxyethyl hydrogen succinate (4.36 mmol) are metered in over a period of 5 minutes. After a reaction time of 2 hours at 70° C., the mixture is cooled to room temperature. 20.9 g of a clear oil having a viscosity of 3814 mm$^2$/s are obtained.

What is claimed is:

1. An ionic organosilicon compound comprising siloxane units of the formula $$A_a R_b X_c SiO_{(4-a-b-c)/2} \quad (I),$$

in which

R is an identical or different, optionally halogenated hydrocarbon radical having 1 to 12 carbon atoms or a radical of the formulae $$-R-((NHCH_2CH_2)_o-(N^+H_2CH_2CH_2)_p-N^{x+g-2)+}H_xR''_q)_{d-1} \quad (II)$$

$$-R'-(SH)_{d-1} \quad (III)$$

or $$-R'-(Z-C(O)-CR'''=CH_2)_{d-1} \quad (IV)$$

in which

R' is an identical or different di-, tri-, or tetravalent hydrocarbon radical having 1 to 60 carbon atoms, which can be interrupted by one or more oxygen atoms, R''' is a hydrogen atom or an alkyl radical having 1 to 8 carbon atoms, Z is an oxygen atom or a radical of the formula $$-NR'''-,$$

R''' is a hydrogen atom or a methyl radical, o is 0 or an integer from 1 to 100, p is 0 or an integer from 1 to 100, q is 0, 1 or 2, x is 0, 1 or 2 and d is 2, 3 or 4, depending on the valency of R', with the proviso that in formula (II) the sum x+q is 2 or 3, X is an identical or different halogen atom or a radical of the formula —OR$^1$, where R$^1$ is an alkyl radical which can be interrupted by an oxygen atom, or a radical of the formula $$-R^2-((CH_2CH_2O)_k-(CH(CH_3)CH_2O)_l-((CH_2)_4O)_m-R^3)_{e-} \quad (V)$$

in which

R$^2$ is a di-, tri- or tetravalent hydrocarbon radical having 1 to 60 carbon atoms, which can be interrupted by one or more oxygen atoms and is substituted by one or more groups of the formulae —C(O)O—, C(O)NR$^3$—, —NR$^3$—, $$-\underset{|}{N}-,$$

—S—, —NH$^+$R$^3$—, $$-\underset{|}{NH^+}-$$

in which

R$^3$ is a hydrogen atom or a hydrocarbon radical having 1 to 30 carbon atoms, which can optionally be interrupted by a group of formula —CO—, k is 0 or an integer from 1 to 100, l is 0 or an integer from 1 to 100, m is 0 or an integer from 1 to 100 and e is 2, 3 or 4, depending on the valency of R$^2$, with the proviso that the sum of k+l+m≧1, and A is a radical of the formula $$-R^4-B_{(f-1)} \quad (VI)$$

in which

R$^4$ has one of the meanings given above for R$^2$, f is 2, 3 or 4, depending on the valency of R$^4$, and B is a radical of the formulae $$-R^5\overset{O}{\underset{\|}{C}}-Z-R^6-SO_3^-,$$

$$-R^5-\overset{O}{\underset{\|}{C}}-Z-R^6-COO^-,$$

$$-R^5-\overset{O}{\underset{\|}{C}}-Z-R^6-OPO_3H_y^{(2-y)-}, \quad -R^5-\overset{O}{\underset{\|}{C}}-O^-,$$

$$-Z-\overset{O}{\underset{\|}{C}}-CHR'''-CH_2-\underset{\underset{R'''}{|}}{N^\oplus H}-R^5-SO_3^-,$$

$$-Z-\overset{O}{\underset{\|}{C}}-CHR'''-CH_2-\underset{\underset{R'''}{|}}{N^\oplus H}-R^5-COO^-,$$

$$-Z-\overset{O}{\underset{\|}{C}}-CHR'''-CH_2-\underset{\underset{R'''}{|}}{N}-R^5-SO_3^-, \text{ or}$$

$$-Z-\overset{O}{\underset{\|}{C}}-CHR'''-CH_2-\underset{\underset{R'''}{|}}{N}-R^5-COO^-,$$

in which

R$^5$ is an identical or different divalent hydrocarbon radical having 2 to 18 carbon atoms, R$^6$ is an identical or different divalent alkyene radical having 1 to 18 carbon atoms or a radical from the group consisting of the formulae $$-CH_2CH_2O\overset{O}{\underset{\|}{C}}-\underset{o,m,p}{\bigcirc},$$

-continued

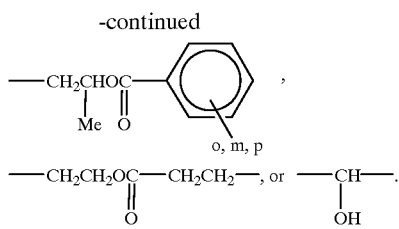

where
Me is the methyl radical,
Z and R''' in each case have one of the meanings given above for these radicals and
y is 0 or 1,
a is 0 or 1,
b is 0, 1, 2 or 3,
c is 0, 1, 2 or 3
and the sum a+b+c is $\leq 4$,
with the proviso that at least one radical A is contained in each molecule.

2. An organosilicon compound as claimed in claim 1, which has an average molecular weight (Mn) of 500 to 1,000,000 g/mole.

3. An organosilicon compound as claimed in claim 1, which has a viscosity of 10 to 1,000,000 mm$^2$/s at 25° C.

4. A process for the preparation of an ionic organsilicon compound as claimed in claim 1, comprising reacting organosilicon compounds of the formula $$R_gX_cSiO_{(4-g-c)/2} \quad (VIII),$$

in which
R, X and c have the meanings given above for these symbols and
g is 0, 1, 2 or 3,
with the proviso that the sum g+c$\leq$4 and the organosilicon compounds contain at least one radical R of formula (II), (III) or (IV) per molecule, with one or more compounds of the formulae

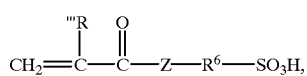 (IX)

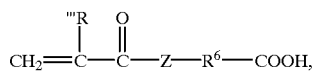 (X)

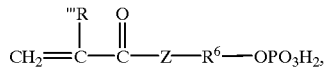 (XI)

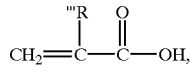 (XII)

if the organosilicon compound contains at least one radical R of formula (II) or (III), or with one or more compounds of the formulae $$R'''NH-R^5-SO_3H \quad (XIII)$$

and $$R'''NH-R^5-COOH \quad (XIV),$$

if the organosilicon compound contains at least one radical R of formula (IV), in which R$^5$ is an identical or different divalent hydrocarbon radical having 2 to 18 carbon atoms, R$^6$ is an identical or different divalent alkylene radical having 1 to 18 carbon atoms or a radical from the group consisting of the formulae

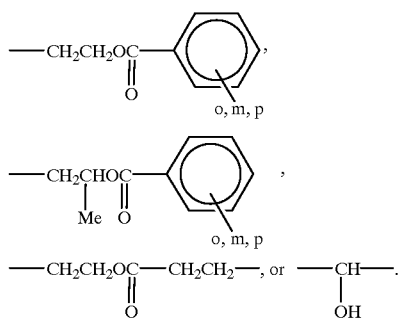

where

Me is the methyl radical,
Z and R''' in each case can be identical or different and have one of the meanings given above for these radicals.

5. The process as claimed in claim 4, wherein organosilicon compounds comprising units of formula (VIII) with radicals R of formula (II) or (IV) are reacted with at least one compound of formula (IX) or (X) or (XIII).

6. The process as claimed in claim 4, wherein organosilicon compounds comprising units of formula (VIII) with radicals R of formula (II) are reacted with at least one compound of formula (IX) or (X).

7. The ionic organosilicon compound as claimed in claim 1, further comprising a non-bonding counter-ion selected from the group consisting of an alkali metal, an alkaline earth and an immonium ion of an organic amine.

8. The ionic organosilicon compound as claimed in claim 1, further comprising a non-bonding counter-ion selected from the group consisting of organic amines.

9. The ionic organosilicon compound as claimed in claim 8, wherein the organic amine is an acetate ion.

* * * * *

UNITED STATES PATENT AND TRADEMARK OFFICE
CERTIFICATE OF CORRECTION

PATENT NO. : 5,990,334
DATED : November 23, 1999
INVENTOR(S) : Hierstetter et al.

It is certified that error appears in the above-identified patent and that said Letters Patent is hereby corrected as shown below:

Column 25, Line 22, Claim 1,

"$-R-((NHCH_2CH_2)_o-(N^+H_2CH_2CH_2)_p-N^{x+g-2)+}H_xR''_q)_{d-1}$"

should be $--R'-((NHCH_2CH_2)_o-(N^+H_2CH_2CH_2)_p-N^{(x+q-2)+}H_xR''_q)_{d-1}--$.

Signed and Sealed this

Twenty-sixth Day of September, 2000

Attest:

Q. TODD DICKINSON

*Attesting Officer*  *Director of Patents and Trademarks*